(12) United States Patent
Hart et al.

(10) Patent No.: US 9,375,228 B2
(45) Date of Patent: Jun. 28, 2016

(54) LAPAROSCOPIC TOOL FOR GRASPING TISSUE

(71) Applicants: Stuart Hart, Tampa, FL (US); Joseph Constantino, Bradenton, FL (US); Susana K. Lai-Yuen, Tampa, FL (US)

(72) Inventors: Stuart Hart, Tampa, FL (US); Joseph Constantino, Bradenton, FL (US); Susana K. Lai-Yuen, Tampa, FL (US)

(73) Assignee: University of South Florida, Tampa, FL (US)

( * ) Notice: Subject to any disclaimer, the term of this patent is extended or adjusted under 35 U.S.C. 154(b) by 364 days.

(21) Appl. No.: 13/919,463

(22) Filed: Jun. 17, 2013

(65) Prior Publication Data

US 2013/0282050 A1    Oct. 24, 2013

Related U.S. Application Data

(63) Continuation of application No. PCT/US2011/065530, filed on Dec. 16, 2011.

(60) Provisional application No. 61/423,833, filed on Dec. 16, 2010.

(51) Int. Cl.
*A61B 17/29* (2006.01)
*A61B 17/08* (2006.01)
(Continued)

(52) U.S. Cl.
CPC ......... *A61B 17/2909* (2013.01); *A61B 17/0401* (2013.01); *A61B 17/29* (2013.01);
(Continued)

(58) Field of Classification Search
CPC .... A61B 17/0401; A61B 17/29; A61B 17/08; A61B 17/083; A61B 17/122; A61B 17/1227; A61B 17/1285; A61B 17/28; A61B 17/2812; A61B 17/282; A61B 2017/00867; A61B 2017/0488; A61B 2017/2931
See application file for complete search history.

(56) References Cited

U.S. PATENT DOCUMENTS 4,485,816 A * 12/1984 Krumme ............ A61B 17/0644
                                                          219/201
4,681,107 A *  7/1987 Kees, Jr. ............ A61B 17/1285
                                                          29/243.56

(Continued)

FOREIGN PATENT DOCUMENTS

EP    2238919 A2    10/2010
WO    9858591 A1    12/1998

OTHER PUBLICATIONS

Stoeckel, Nitinol medical devices and implants. Min Invas Ther & Allied Technol. 2000. vol. 9 (Issue 2):81-88.
(Continued)

*Primary Examiner* — Sarah W Aleman
(74) *Attorney, Agent, or Firm* — Nilay J. Choksi; Jeremy Spier; Smith & Hopen, P.A.

(57) ABSTRACT

A laparoscopic tool includes a base having a bore that receives the proximal end of an elongate outer tube having a lumen in axial alignment with the bore. An elongate inner rod is slideably mounted in the lumen and the bore. A clamp is detachably secured to a distal end of the elongate inner rod. A handle controlled by a user advances and retracts the inner rod. A nitinol clamp is connected to the distal end of the inner rod and an electrically conductive suture thread holds the clamp to the inner rod. A wedge block positioned at the proximal end of the inner rod has a slit that releasably engages the suture thread so that the suture thread is pulled until it is taut and wedged into the slit. The clamp closes when heated by an electrical current flowing through the suture thread and opens when the current stops.

8 Claims, 6 Drawing Sheets

(51) Int. Cl.
*A61B 17/122* (2006.01)
*A61B 17/04* (2006.01)
*A61B 17/00* (2006.01)

(52) U.S. Cl.
CPC ............ *A61B 17/083* (2013.01); *A61B 17/122* (2013.01); *A61B 2017/00265* (2013.01); *A61B 2017/00734* (2013.01); *A61B 2017/00867* (2013.01); *A61B 2017/0409* (2013.01); *A61B 2017/0446* (2013.01); *A61B 2017/0464* (2013.01); *A61B 2017/2931* (2013.01)

(56) References Cited

U.S. PATENT DOCUMENTS

| | | |
|---|---|---|
| 5,449,365 A | 9/1995 | Green et al. |
| 5,769,848 A | 6/1998 | Wattanasirichaigoon |
| 5,776,147 A | 7/1998 | Dolendo |
| 2003/0167063 A1 | 9/2003 | Kerr |
| 2004/0092957 A1 | 5/2004 | Lippitt et al. |
| 2007/0156171 A1 | 7/2007 | Lang et al. |
| 2009/0143816 A1 | 6/2009 | Boyden et al. |
| 2010/0249498 A1* | 9/2010 | Wingardner ......... A61B 17/122 600/104 |

OTHER PUBLICATIONS

Shurr et al., The OTSC clip for endoscopic organ closure in NOTES: device and technique. Minimally Invasive Therapy. 2008. vol. 17 (Issue 4):262-266.

Duerig et al., An overview of nitinol medical applications. Materials Science and Engineering. 1999. vol. A273-275:149-160.

International Search Report for PCT/US2011/065530 (filing date: Dec. 16, 2011) with a mailing date of Jul. 18, 2012; Applicant: University of South Florida et al.

Preliminary Report on Patentability for PCT/US2011/065530 (filing date: Dec. 16, 2011) with a priority date of Dec. 16, 2010; Applicant: University of South Florida et al.

* cited by examiner

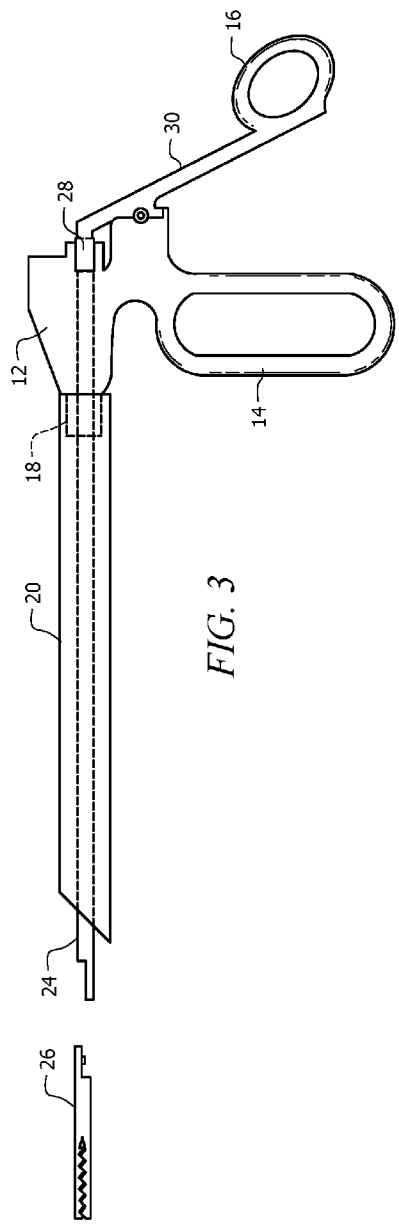
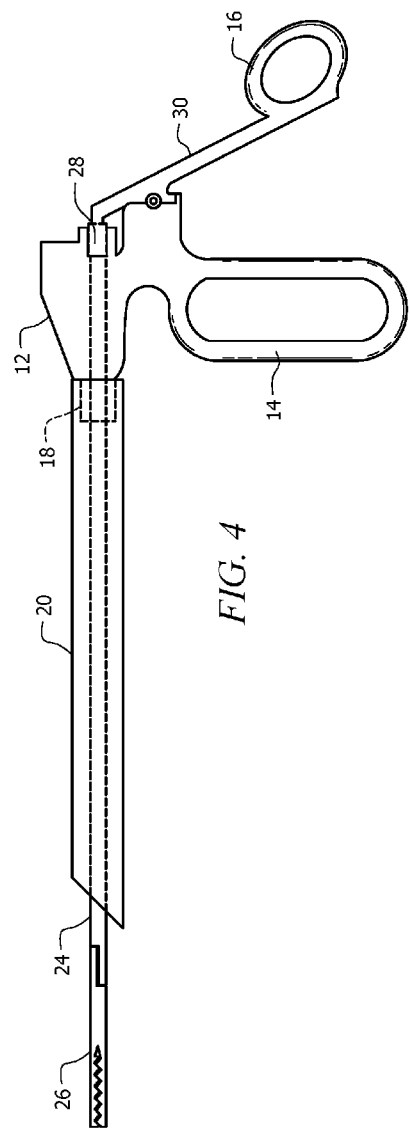

LAPAROSCOPIC TOOL FOR GRASPING TISSUE

BACKGROUND OF THE INVENTION

1. Field of the Invention

This invention relates, generally, to surgical instruments. More particularly, it relates to a surgical tool having utility in laparoscopic procedures.

2. Description of the Prior Art

Laparoscopic surgery is minimally invasive and is the standard for performing numerous surgical procedures across various surgical specialties. An incision is made in the umbilicus or other area of the abdomen for insertion of a port containing a camera device for visualization during laparoscopic surgery. Placement of laparoscopic instruments during laparoscopic surgery requires the creation of multiple skin incisions with a scalpel, and then placement of laparoscopic ports. Multiple laparoscopic instruments can then be passed through each laparoscopic port to perform the surgical procedure. Typically, three to four laparoscopic ports must be placed during conventional laparoscopic surgery. Typically, laparoscopic ports range from 5 to 12 mm in diameter, leave abdominal scars, and contribute to post-operative pain.

Laparo-Endoscopic Single Site (LESS) surgery has been introduced as a means to perform minimally invasive surgery without noticeable abdominal incisions, and to improve post-operative pain. LESS surgery is performed entirely through a single incision in the umbilicus.

LESS surgery eliminates the need for multiple incisions during laparoscopic surgery, but also creates many challenges. Since the surgery is performed entirely through a single umbilical incision, and because the instruments must be in close proximity to each other, the ability to manipulate instruments during surgery is limited. "Sword fighting" occurs when the instruments continually collide, and such interference contributes to inefficient surgical movements and procedures. Moreover, LESS surgery eliminates triangulation, which occurs when instruments are inserted into the abdomen at multiple port sites at varying angles to facilitate visualization and tissue manipulation.

These challenges ultimately increase surgical operative time and reduce the efficiency of the surgery, and may serve as a significant obstacle to widespread adoption of the LESS technique by surgeons.

Thus, there is a need for a tool that is easily controllable, which, in turn, reduces collisions with other instruments during laparoscopic procedures. There is also a need for a tool that is easy to control so that it can be used to triangulate with other tools.

However, in view of the art considered as a whole at the time the present invention was made, it was not obvious to those of ordinary skill in the art how the needed tool could be provided.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved tissue-grabbing clamp for use in laparoscopic surgery is now met by a new, useful, and non-obvious invention.

The novel device assists surgeons in the performance of laparoscopic and laparo-endoscopic surgery. It enables tissue to be grasped for appropriate surgical manipulation during a surgical procedure, without the need for an endomechanical laparoscopic instrument, by using electrically conductive insulated suture thread for manipulation. This contributes to less abdominal wall trauma and preservation of triangulation, which is often lost in the performance of laparo-endoscopic single site surgery. It also allows control of tissue using an electrically controlled clamp, and a suture thread, with the ability to detach the clamp from the tissue without the need for an endomechanical laparoscopic device.

In an embodiment, a laparoscopic tool includes a solid base (e.g., handle) having a longitudinally-extending bore formed therein, an elongate outer tube secured to the base and having a lumen in axial alignments and in open communication with the bore, and an elongate inner rod slideably mounted in the lumen of the outer tube within the bore. The proximal end of the inner rod extends proximally from the bore and thus can be engaged by a user to extend the inner rod in a forward direction or retracted direction. The tool also includes a clamp that is formed of a memory alloy and is detachably connected to the distal end of the inner rod. The tool also includes an electrically-conductive suture thread that holds the clamp to the inner rod. The inner rod and the clamp have a combined length that when the tool is engaged and the inner tube and clamp are disposed within the lumen of the outer tube and the bore, the distal end of the clamp extends beyond the distal end of the outer tube. Conversely, when the tool is disengaged and the inner tube and clamp are disposed within the lumen of the outer tube and the bore, the distal end of the outer tube extends beyond the distal end of the clamp. This allows the outer tube to pierce the skin of a subject when the tool is disengaged. The tool also includes a source of electrical power that is in switched electrical communication with the electrically-conductive suture thread. The clamp has two positions, an open position and closed position, wherein a change between the two positions is heat activated. Heat is generated when current flows through the electrically-conductive suture thread.

The memory alloy forming the clamp may be a pseudo-elastic metal.

Engagement of the proximal end of the inner rod can be accomplished manually, mechanically, pneumatically, electro-mechanically, or electro-magnetically.

The clamp may be openable and closable only when the inner rod is fully advanced in the forward direction, so that the clamp is external to the lumen of the outer tube.

The current may be activated and deactivated by a switch actuator mounted on the handle.

The electrically-conductive suture thread may be disposed within the lumen of the elongate outer tube.

The tool may include an elongate slit formed in the outer tube to enable removal of the electrically-conductive suture thread from the lumen of the outer tube, so that the suture thread and the clamp can be used for surgical procedures after the outer tube is removed from the body of a patient.

The tool may also include a wedge block formed in the proximal end of the inner tube and a slit formed in the wedge block. The slit is adapted to releasably engage the electrically-conductive suture thread. The suture thread can be pulled in a retracted direction until it is taut and wedged into the slit to maintain the suture thread in taut condition.

The handle may include a finger grip and a thumb grip. The thumb grip would be disposed proximally to the finger grip. The thumb grip would be mounted for pivotal movement in a plane occupied by the handle. When the thumb grip is moved in a retracted direction, the inner rod can move in the forward direction. When the thumb grip is moved in a forward direction, the inner rod can move in the retracted direction.

In a separate embodiment, a tool used in laparoscopic procedures for grasping tissue internal to a patient includes a solid base (e.g., handle) having a longitudinally-extending bore formed therein, an elongate outer tube secured to the base and having a lumen in axial alignments and in open communication with the bore, and an elongate inner rod slideably mounted in the lumen of the outer tube within the bore. The proximal end of the inner rod extends proximally from the bore and thus can be engaged by a user to extend the inner rod in a forward direction or retracted direction. The tool also includes a wedge block formed in the proximal end of the inner tube and a slit formed in the wedge block. The slit is adapted to releasably engage the electrically-conductive suture thread. The suture thread can be pulled in a retracted direction until it is taut and wedged into the slit to maintain the suture thread in taut condition. The tool also includes a clamp that is formed of a memory alloy and is detachably connected to the distal end of the inner rod. The tool also includes an electrically-conductive suture thread that holds the clamp to the inner rod. The inner rod and the clamp have a combined length that when the tool is engaged and the inner tube and clamp are disposed within the lumen of the outer tube and the bore, the distal end of the clamp extends beyond the distal end of the outer tube. Conversely, when the tool is disengaged and the inner tube and clamp are disposed within the lumen of the outer tube and the bore, the distal end of the outer tube extends beyond the distal end of the clamp. This allows the outer tube to pierce the skin of a subject when the tool is disengaged. The clamp is openable and closable only when the inner rod is fully advanced in the forward direction, so that the clamp is external to the lumen of the outer tube. The tool also includes an elongate slit formed in the outer tube to enable removal of the electrically-conductive suture thread from the lumen of the outer tube, so that the suture thread and the clamp can be used for surgical procedures after the outer tube is removed from the body of a patient. The tool also includes a source of electrical power that is in switched electrical communication with the electrically-conductive suture thread. The clamp has two positions, an open position and closed position, wherein a change between the two positions is heat activated. Heat is generated when current flows through the electrically-conductive suture thread. The current is activated and deactivated by a switch actuator mounted on the handle.

The primary object of the invention is to advance the art of laparoscopic surgery.

A more specific object is to advance said art by providing a tool that facilitates the grasping and releasing of tissue during surgery.

Another object is to provide a tool that harnesses the properties of nitinol and other shape memory alloys.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 3 is a side elevational view of a laparoscopic tool depicting the sawtooth clamp separated from the inner rod;

FIG. 4 is a side elevational view of a laparoscopic tool depicting the sawtooth clamp connected to the inner rod;

DETAILED DESCRIPTION OF THE PREFERRED EMBODIMENT

Figure 1:
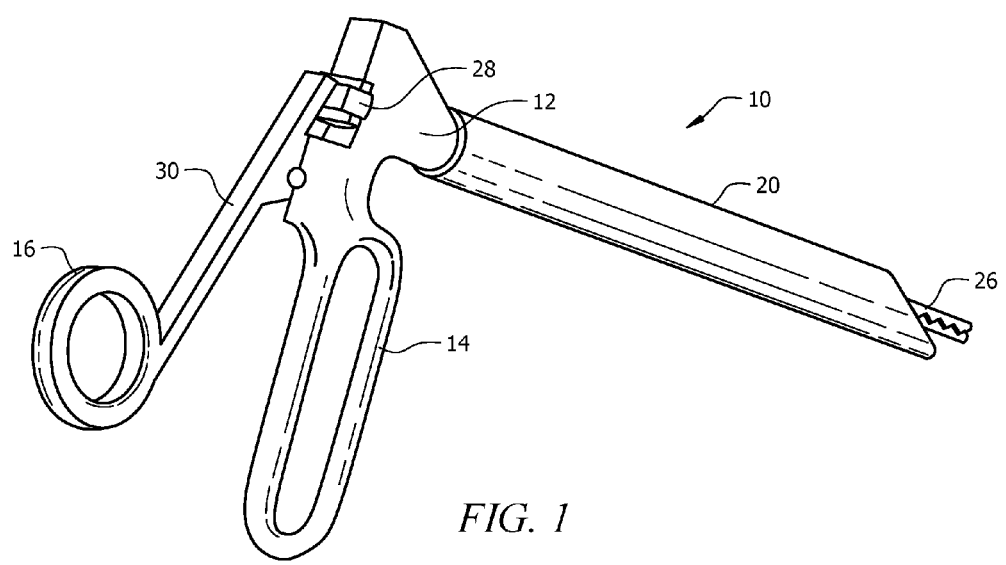
FIG. 1 is a perspective view of a laparoscopic tool when its inner rod and clamp are fully advanced and the clamp is in its normally closed configuration.
Figure 2:
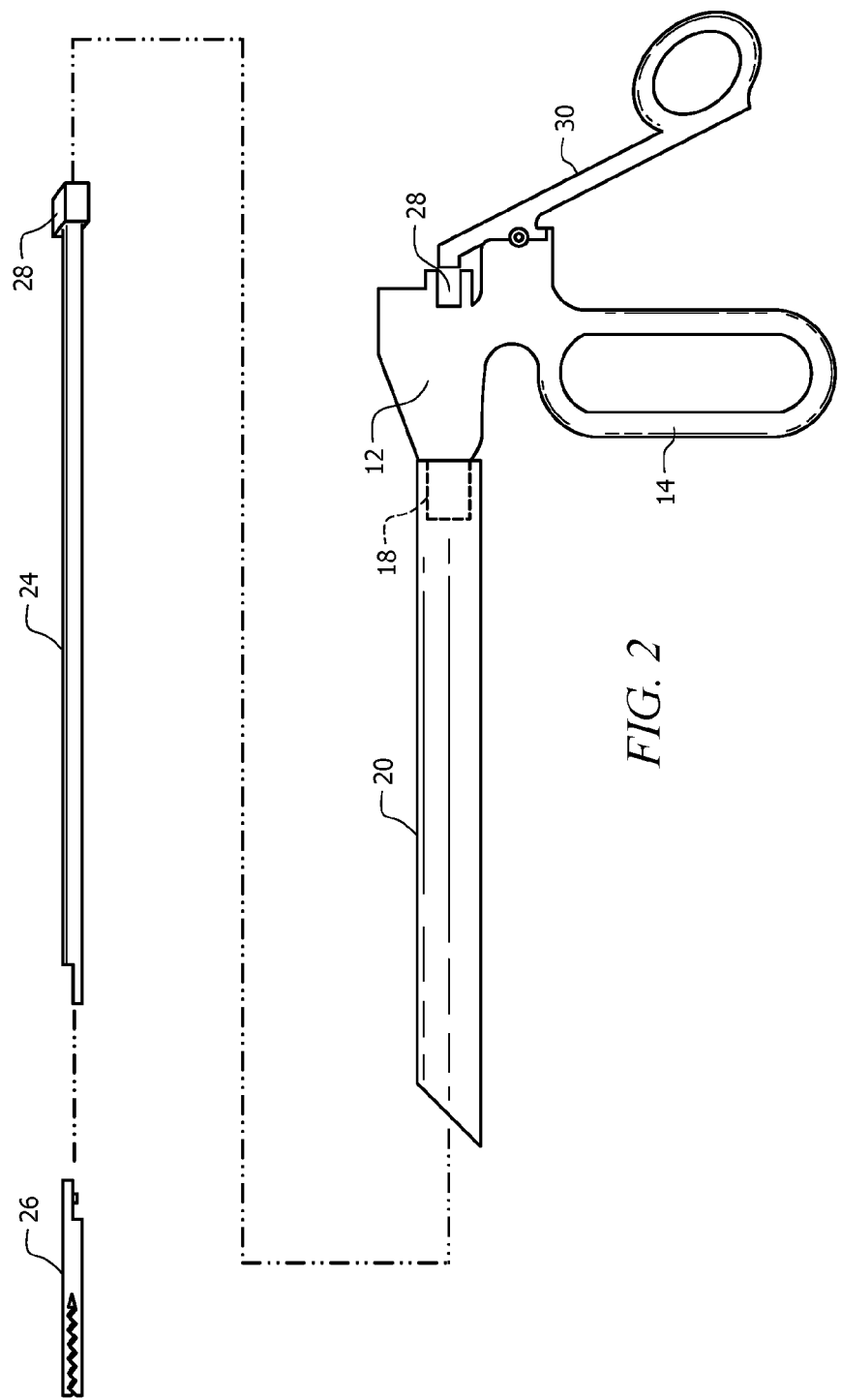
FIG. 2 is a side elevational, assembly view of a laparoscopic tool.
Figure 5:
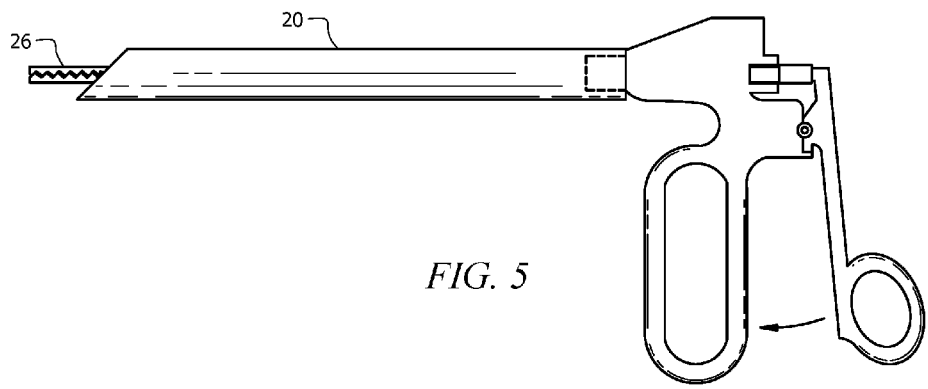
FIG. 5 is a side elevational view depicting a laparoscopic tool when the handle is in a neutral position.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The novel device assists surgeons in the performance of laparoscopic and laparo-endoscopic surgery. It enables tissue to be grasped for appropriate surgical manipulation during a surgical procedure, without the need for an endomechanical instrument, by using electrically conductive insulated suture thread for manipulation. This contributes to less abdominal wall trauma and preservation of triangulation, which is often lost in the performance of laparo-endoscopic single site surgery. It also allows control of tissue using an electrically controlled clamp, and a suture thread, with the ability to detach the clamp from the tissue without the need for an endomechanical laparoscopic device.

The novel laparoscopic clamp instrument is placed into an abdomen without creation of a skin incision. The shaft or outer tube of the laparoscopic instrument can be 2.1 mm in diameter with a beveled end, resembling a fourteen (14) gauge intravenous needle. The beveled end is placed into the abdomen similar to the placement of a needle, without creation of a skin incision with a scalpel, and without the need for a laparoscopic port placement.

When the outer tube is inside the body, the surgeon attaches a clamp formed of nitinol or other shape memory alloy, which may be one-way metal or two-way metal, to an organ or tissue, using a handle to guide the clamp towards the tissue. The clamp has a normally closed configuration. If a one-way metal is used, the surgeon can engage an inner rod disposed within the outer tube and proximally connected to the clamp. Once engaged, the clamp extends beyond the distal end of the outer tube, and the surgeon can press a button formed on a handle to close a switch that completes a circuit so that electrical current flowing through the suture thread generates heat sufficient to warm the nitinol, which, in turn, causes closing of the clamp. After the clamp grasps the tissue, it can be opened by pressing the button a second time, or pressing a second button a first time, to open the electrical circuit. The clamp can returns to its normally closed position when the surgeon manually presses the clamp closed.

Tissue is grasped when the jaws of the clamp are opened and subsequently closed around the tissue. The jaws of the clamp can be opened to release the grasped tissue after such grasping is no longer required by the surgical procedure by closing the electrical circuit so that electricity warms the nitinol, causing it to open. When the tissue is released, the user can close the clamp to form its normally closed configuration by pressing it under its inherent bias.

The nitinol clamp can also be removed with the surgical specimen at the end of the surgical procedure. The clamp is removed with an attached electrically conductive insulated suture thread when the jaws are their closed position.

Certain embodiments of the laparoscopic tool are designed to deploy a detachable, stand-alone clamp capable of opening and closing using a combination of two-way, pseudo-elastic metal and electricity to control the motion. The nitinol clamp may also include FLEXINOL® shape memory alloy, representing the pre-crimped part of the nitinol clamp, which enables the connection of the electrically conductive suture thread to a source of electrical power. The FLEXINOL® alloy forms the top and bottom halves of the clamp where the opening and closing occurs. Closing and opening of the clamp is achieved through contraction and expansion of the FLEXINOL® alloy upon heat activation and deactivation.

The outer tube which serves as an entry needle and the inner rod part of the device can be removed after the clamp is attached to tissue. This results in the clamp attached to the targeted tissue, with the electrically conductive insulated suture thread acting as suture thread running up through the puncture site for control of the tissue.

The end of the insulated suture thread has an electrical connection in the form of a plug that allows it to be quickly connected to or disconnected from the handle so that the clamp can be opened and closed. The insulated suture thread that provides an interface between the clamp and the handle can also be retrieved through the outer tube if needed. A slit is formed along the extent of the elongate outer tube to facilitate such retrieval.

If the outer tube and inner rod are disassembled after attachment of the nitinol grasper to tissue, the insulated suture thread is detached from the handle and removed from the tube. The clamp and attached tissue can then be controlled by manipulation of the insulated suture thread outside the abdomen, or the electrical connection plug can be reconnected to the handle to control opening of the clamp through the electrical source.

The novel device is modular so that if the device is disassembled and reassembled, the user is still able to use the suture thread connected to the clamp to manipulate the grasped organs or tissue manually. If a user removes the suture thread connected clamp from the rest of the assembly, such action is facilitated by the structural features of the novel tool. The novel tool allows the desired action of manipulating organs via the suture thread attached clamp to either be a standalone feature where the organs are manipulated manually by hand or such manipulation may remain an action controlled by the handle via the quick connect/disconnect plug or any other parts remaining assembled to the tool. The entire device can thus perform desired functions when fully assembled or partially disassembled.

The outer diameter of the electrical plug can be substantially equal to the outer diameter of the inner rod such that the electrical plug fits within the lumen of the outer tube and the lumen of a bore formed in the handle for easy removal. The surgeon can control the clamp and desired tissue by manipulation of the suture thread, or use of the handle, outside the abdomen. The electrical plug may also be positioned on the handle of the tool.

The nitinol clamp is in axial alignment with the outer tube and is attached to the distal end of the inner rod. The clamp is supported radially at all times because it does not fully exit the lumen of the outer tube. The support constrains the clamp from translation in both axes perpendicular to the longitudinal axis of symmetry of the rod and clamp. When the rod and clamp are engaged axially through the mechanically constrained full range of motion, this range of motion prevents the clamp from entering into an axial position such that the clamp is no longer supported by the tube. This range of motion extends to a minimum such that the opening of the clamp is not constrained by the tube. The rod adds additional structural support in addition to constraining rotation about the longitudinal axis of symmetry with respect to the clamp through the incorporation of the features associated at the locations mating the two parts. These features ensure conjoint rotation of both parts. The clamp and inner rod subassembly may also incorporate a feature to constrain rotation about the longitudinal axis of symmetry with respect to the handle and tube.

The clamp can be supported axially by the taut suture thread that runs through a groove formed in the inner rod and held in place by a slit or wedged groove formed in a wedge block that is formed in the proximal end of the inner rod. The wedged groove acts as a suture thread tensioner that holds the clamp to the rod axially. The plug is connected by suitable means to the proximal end of the suture thread. Such suitable means may include a standard UL-approved socket connector having a first end attached to the suture thread and a second end formed in the handle.

The FLEXINOL® alloy deforms (contracts/expands) upon power delivery, driving the top half upward and bottom half downward. The FLEXINOL® alloy can have two learned positions, the open and closed positions, which are heat-activated.

The tool can be made in any suitable length. The electrical wire gauge is preferably 22 AWG (0.65 mm diameter) but such gauge is not critical.

More particularly, the novel laparoscopic tool includes a solid base having a longitudinally-extending bore formed therein. An elongate outer tube is secured to the base. The elongate outer tube has a lumen in axial alignment and in open communication with the bore.

An elongate inner rod is slideably mounted in the lumen of the elongate outer tube and within the bore and a clamp is detachably secured to a distal end of the elongate inner rod. A handle controlled by a user advances the elongate inner rod in a proximal-to-distal direction and retracts the inner rod in a distal-to-proximal direction.

A nitinol clamp is connected to the distal end of the elongate inner rod and an electrically-conductive suture thread holds the nitinol clamp to the elongate inner rod. A wedge block can be positioned at a proximal end of the inner rod and have a slit formed therein that is adapted to releasably engage the suture thread. The suture thread can be pulled in a distal-to-proximal direction until it is taut and is wedged into the slit to maintain the suture thread in the taut condition.

The elongate inner rod and clamp have a combined length such that when the tool is engaged and the inner tube and clamp are disposed within the lumen of the outer tube and the bore, the distal end of the clamp extends beyond the distal end of the outer tube. When the tool is disengaged, though, and the inner tube and clamp are disposed within the lumen of the outer tube and the bore, the distal end of the outer tube extends beyond the distal end of the clamp. This would allow the outer tube to pierce the skin of a subject when the tool is disengaged.

It is also contemplated that the clamp can be opened and closed only when the elongate inner rod is fully advanced in the proximal-to-distal direction, i.e., when the clamp is external to the lumen of the elongate outer tube.

The clamp closes when heated by an electrical current flowing through the electrically-conductive suture thread or compressed by a user and opens when the current and hence the heat are removed. The current can be activated and deactivated by a button mounted on the handle.

An elongate slit formed in the elongate outer tube may be formed to enable removal of the suture thread from the elongate outer tube so that the suture thread and the nitinol clamp can continue to be used even when the tool including the handle and the elongate outer tube are removed from the body of a patient.

Example 1

FIG. 1 depicts a first illustrative embodiment of the novel tool, denoted as a whole by the reference numeral 10. The electrically-conductive insulated suture thread that is coupled to the nitinol clamp to cause it to close when heated by electrical current is not depicted in this first embodiment.

Hand-held tool 10 includes flat base 12 that is formed integrally with finger grip 14. Thumb grip 16 is formed separately in this first embodiment and is mounted for pivotal movement in the plane occupied by base 12. Finger grip 14 has a loop shape to accommodate fingers that are inserted into the area bordered by the loop when tool 10 is held. Thumb grip 16 has a generally circular shape and accommodates a thumb so that tool 10 may be held in a well-known way.

A cylindrical boss, not depicted, is integrally formed in a distal end of flat base 12 and the proximal end of elongate outer tube 20 is secured to said boss. The boss is received within lumen 18 of outer tube 20 and may be fixedly secured thereto by an adhesive or by other suitable means. Alternatively, as depicted in connection with a second embodiment disclosed hereinafter, the boss is eliminated and a bore 22 is formed in the distal end of base 12 to accommodate the proximal end of outer tube 20. An adhesive or other suitable means may be employed to secure the connection between base 12 and outer tube 20.

Figure 6:
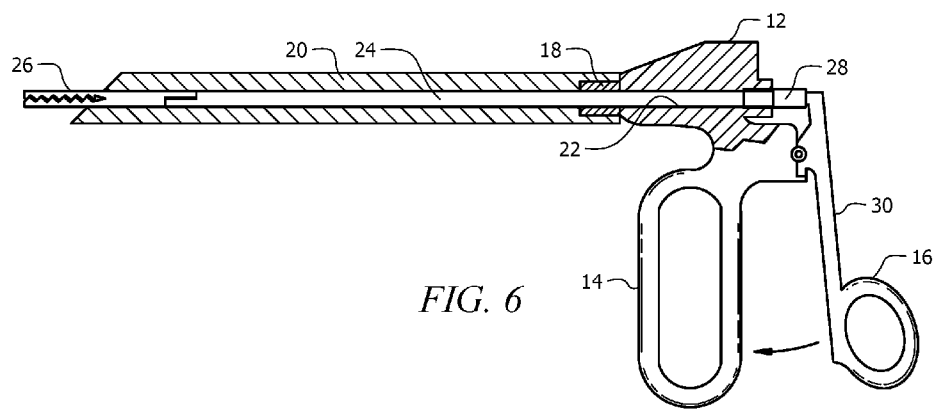
FIG. 6 is a partial sectional view of the structure depicted in FIG. 5.
Figure 7:
FIG. 7 is a perspective view of a laparoscopic tool depicting how the inner rod and sawtooth clamp are connected to one another.

As depicted in FIGS. 3, 4, and 6, bore 22 is formed in base 12 in axial alignment with lumen 18 of outer tube 20 and is in open communication therewith. Inner rod 24 is slideably received within said bore 22 and lumen 18 as suggested by the assembly line in FIG. 1.

Inner rod 24 is slideably disposed within lumen 18, and a distal end of inner rod 24 is connected to a proximal end of nitinol clamp 26. The connection between inner rod 24 and nitinol clamp 26 is a soft connection, i.e., there is no locking mechanism associated with the mating of clamp 26 and inner rod 24. The support and constraint of six degrees of freedom are achieved through the outer tube 20 providing radial support (two (2) translational degrees of freedom and two (2) rotational degrees of freedom), the clamp-to-inner rod interface or mating that allows said two (2) parts to rotate conjointly about their common longitudinal axis of symmetry, thereby eliminating the third rotational degree of freedom of inner rod 24. The clamp-to-rod interface also adds additional support within outer tube 20, independent of the tube, to gravitational or other forces perpendicular to said common axis of symmetry. The sixth and final degree of freedom is the conjoint translation of inner rod 24 and clamp 26 coincident with the common axis of symmetry.

The clamp-to-rod axial interface is also supported by the suture thread which holds clamp 26 to inner rod 24 by means of wedge block 28 at the proximal end of inner rod 24. The suture thread is pulled in a distal-to-proximal direction, i.e., toward the user or toward the device handle, until it is taut. The suture is then wedged into slit 28a formed in wedge block 28 to maintain that tautness. The suture thread thus acts as a tensioner that holds clamp 26 to inner rod 24. Movement into and out of outer tube 20 for the clamp and rod connection is necessary for proper device operation.

The combined length of inner rod 24 and clamp 26 have a combined length such that when tool 10 is engaged and inner rod 24 and clamp 26 are disposed within lumen 18 of outer tube 20 and bore 22, the distal end of clamp 26 extends beyond the distal end of outer tube 20. Conversely, when tool 10 is disengaged and inner rod 24 and clamp 26 are disposed within lumen 18 of outer tube 20 and bore 22, the distal end of outer tube 20 extends beyond the distal end of clamp 26. This allows outer tube 20 to pierce the skin of a subject when tool 10 is disengaged.

Wedge block 28 is fixedly secured to or integrally formed with the proximal end of inner rod 24 and is hingedly engaged by arm 30 that is formed integrally with thumb grip 16. Thumb movement in a distal-to-proximal direction pushes wedge block 28 and hence inner rod 24 forwardly, i.e., in a proximal-to-distal direction and thumb movement in a proximal-to-distal direction pulls wedge block 28 and hence inner rod 24 rearward, i.e., in a distal-to-proximal direction. Such rearward movement retracts clamp 26 into the lumen 18 of outer tube 20.

Clamp 26 is openable and closable only when inner rod 24 is fully advanced in said proximal-to-distal direction, i.e., when clamp 26 is external to lumen 18 of outer tube 20. Clamp 26 closes when heated by an electrical current or manually compressed by a user and open when the current and hence the heat are removed. The current can be activated and deactivated by a button mounted on the handle.

Example 2

Figure 8:
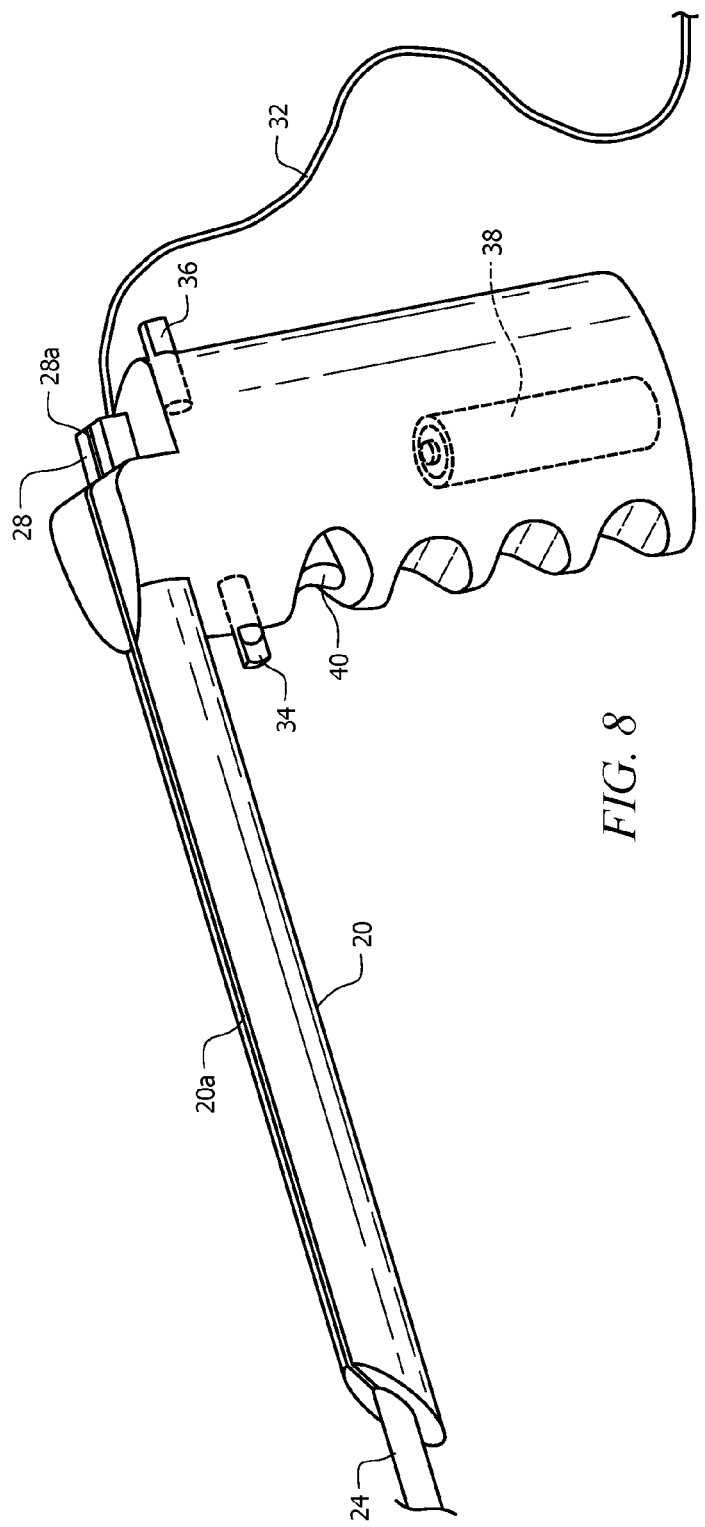
FIG. 8 is a perspective view of a laparoscopic tool.
Figure 9:
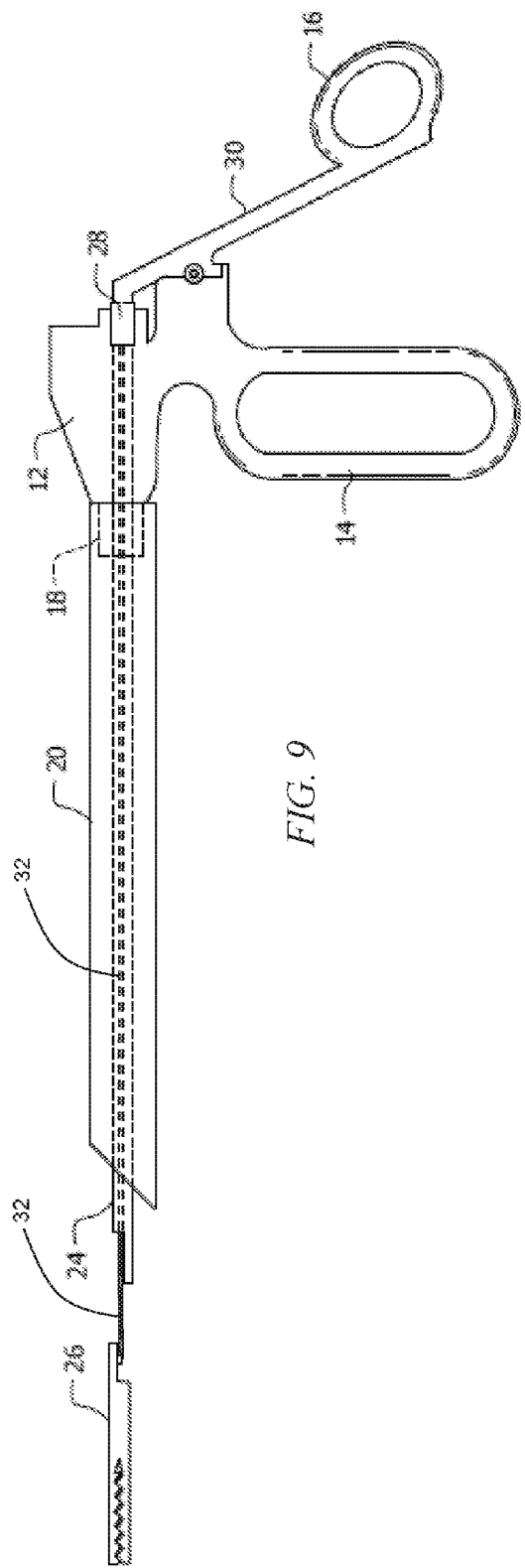
FIG. 9 is a side cross sectional view of a laparoscopic tool with suture disposed within the lumen of the elongate outer tube.

A second embodiment is depicted in FIG. 8. Suture thread 32 is depicted in this embodiment, as is slit 20a formed in outer tube 20 that enables suture thread 32 and clamp 26 to remain in a patient's body when outer tube 20 is removed therefrom. It should be understood that the connection of suture thread 32 with wedge block 28 and slit 28a as depicted in this second embodiment works in the same way as in the first embodiment where the suture thread was not depicted. The disposition of suture thread 32 from wedge clamp 28 to clamp 26 through outer lumen 20 can be seen in FIG. 9.

Electrical plugs 34 and 36 are electrically connected to the handle. They provide an interface for connecting electrically conductive suture thread 32 to said handle. Although two plugs are depicted, one on the front and one on the back of the handle, only one would be provided in a commercial embodiment. The interface could also be provided in the form of crimp connects, soldered connections, and the like.

In the embodiment of FIG. 8, inner rod 24 is manually displaced within the lumen of elongate outer tube 20. However, it could also be manipulated by the pivoted finger and thumb handle arrangement of the first embodiment or by other mechanical or electromechanical means.

Item 38 is a battery disposed within hollow handle. Button 40 is a switch actuator that controls a switch that opens and closes the electrical circuit that sends current from said battery to plug 34 or 36 and through suture thread 32 when closed.

The novel device advances the art of minimally invasive surgery by incorporating a pseudo-elastic material allowing the overall medical device to efficiently manipulate organs while producing minimal footprints such as scars or pain, while facilitating the performance of the innovative and complex procedures of laparoscopic practice.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A laparoscopic tool, comprising:
a solid base in the form of a handle having a longitudinally-extending bore formed therein;
an elongate outer tube secured to said base, said elongate outer tube having a lumen in axial alignment and in open communication with said bore;
an elongate inner rod slideably mounted in said lumen of said elongate outer tube and within said bore;
a proximal end of said elongate inner rod being engageable by a user of said tool to selectively slide said elongate inner rod in a proximal-to-distal forward or extended direction and a distal-to-proximal rearward or retracted direction;
a clamp, formed of a memory alloy, detachably secured to a distal end of said elongate inner rod;
a longitudinally-extending, electrically-conductive suture thread holding said clamp to said distal end of said elongate inner rod, said suture thread is disposed within said lumen of said elongate outer tube;
said elongate inner rod and clamp having a combined length such that when said elongate inner rod is slideably disposed within said lumen and said bore in an engaged or extended position, the distal end of said clamp extends beyond the distal end of said elongate outer tube, and when said elongate inner rod is slideably disposed within said lumen and said bore in a disengaged or retracted position, the distal end of said elongate outer tube extends beyond the distal end of said clamp;
an elongate slit formed in said elongate outer tube to enable removal of said electrically-conductive suture thread from said lumen of said elongate outer tube so that said electrically-conductive suture thread and said clamp can be used for surgical procedures after said elongate outer tube is removed from the body of a patient;
a source of electrical power;
said electrically-conductive suture thread being in switched electrical communication with said source of electrical power;
said clamp having two positions, an open position and a closed position, wherein a change between said two positions is heat activated.

2. The tool of claim 1, wherein:
said engagement of said proximal end of said tool by said user is selected from the group consisting of manual engagement, mechanical engagement, pneumatic engagement, electro-mechanical engagement, and electro-magnetic engagement; and
said handle of said tool is suitable for said selected engagement by said user.

3. The tool of claim 1, wherein:
said memory alloy is a pseudo-elastic metal.

4. The tool of claim 1, wherein:
said clamp is openable and closable only when said elongate inner rod is fully advanced in said proximal-to-distal direction so that said clamp is external to said lumen of said elongate outer tube.

5. The tool of claim 1, wherein:
said heat is activated and deactivated by a switch actuator mounted on said handle.

6. The tool of claim 1, further comprising:
a wedge block formed in said elongate inner tube at said proximal end thereof;
a slit formed in said wedge block, said slit adapted to releasably engage said electrically-conductive suture thread;
said suture thread being pulled in a distal-to-proximal direction until it is taut and being wedged into said slit to maintain said suture thread in said taut condition.

7. The tool of claim 1, wherein:
said handle includes a finger grip and a thumb grip, said thumb grip disposed proximally to said finger grip, said finger grip and said thumb grip mounted for pivotal movement in a plane occupied by said handle, whereby when said thumb grip is moved in a distal-to-proximal direction, said inner rod moves in said proximal-to-distal direction, and when said thumb grip is moved in a proximal-to-distal direction, said inner rod moves in said distal-to-proximal direction.

8. A tool used in laparoscopic procedures for grasping tissue internal to a patient, comprising:
a solid base in the form of a handle having a longitudinally-extending bore formed therein;
an elongate outer tube secured to said base, said elongate outer tube having a lumen in axial alignment and in open communication with said bore;
an elongate inner rod slideably mounted in said lumen of said elongate outer tube and within said bore;
a proximal end of said elongate inner rod extending proximally from said longitudinally-extending bore, said proximal end being manually engageable by a user of said tool to selectively slide said elongate inner rod in a proximal-to-distal forward or extended direction and a distal-to-proximal rearward or retracted direction;

a clamp, formed of a pseudo-elastic metal, detachably secured to a distal end of said elongate inner rod;

a longitudinally-extending, electrically-conductive suture thread disposed within said lumen of said elongate outer tube, said suture thread holding said clamp to said distal end of said elongate inner rod;

a wedge block formed in said elongate inner tube at said proximal end thereof;

a slit formed in said wedge block, said s adapted to releasably engage said electrically-conductive suture thread;

said suture thread being pulled in a distal-to-proximal direction until it is taut and being wedged into said slit to maintain said suture thread in said taut condition;

an elongate slit formed in said elongate outer tube to enable removal of said electrically-conductive suture thread from said lumen of said elongate outer tube so that said electrically-conductive suture thread and said clamp can be used for surgical procedures after the elongate outer tube is removed from the body of said patient;

said elongate inner rod and clamp having a combined length such that when said elongate inner rod is slideably disposed within said lumen and said bore in an engaged or extended position, the distal end of said clamp extends beyond the distal end of said elongate outer tube, and when said elongate inner rod is slideably disposed within said lumen and said bore in a disengaged or retracted position, the distal end of said elongate outer tube extends beyond the distal end of said clamp;

said clamp being openable and closable only when said elongate inner rod is fully advanced in said proximal-to-distal direction so that said clamp is external to said lumen of said elongate outer tube;

a source of electrical power;

said electrically-conductive suture thread being in switched electrical communication with said source of electrical power;

said clamp having two positions, an open position and a closed position, wherein a change between said two positions is heat activated; and said source of electrical power being activated and deactivated by a switch actuator mounted on said handle.

* * * * *